United States Patent [19]
Losch et al.

[11] Patent Number: 5,310,734
[45] Date of Patent: May 10, 1994

[54] PHOSPHOLIPID COMPOSITION

[75] Inventors: Rainer Losch, Bonn; Bernd-Rainer Günther, Bergheim; Jörg Hager, Cologne, all of Fed. Rep. of Germany

[73] Assignee: Rhone-Poulenc Rorer, Cologne, Fed. Rep. of Germany

[21] Appl. No.: 906,620

[22] Filed: Jun. 30, 1992

[30] Foreign Application Priority Data

Jul. 5, 1991 [DE] Fed. Rep. of Germany ....... 4122300
Jun. 17, 1992 [DE] Fed. Rep. of Germany ....... 4219715

[51] Int. Cl.$^5$ ................... A61K 31/685; A61K 47/60
[52] U.S. Cl. ........................................ 514/78; 424/439
[58] Field of Search .......................... 514/78; 424/439

[56] References Cited

U.S. PATENT DOCUMENTS

| | | | |
|---|---|---|---|
| 2,057,695 | 10/1936 | Schwieger | 424/78 |
| 3,012,838 | 12/1961 | Davis et al. | 424/78 |
| 4,762,658 | 8/1988 | Rothfuss et al. | 264/122 |

FOREIGN PATENT DOCUMENTS

| | | | |
|---|---|---|---|
| 0054770 | 6/1982 | European Pat. Off. | A23J 7/00 |
| 0054769 | 12/1984 | European Pat. Off. | A23J 7/00 |
| 973741 | 5/1960 | Fed. Rep. of Germany | |
| 3826946 | 3/1990 | Fed. Rep. of Germany | A61K 47/00 |

OTHER PUBLICATIONS

Rompp Chemie Lexikon, edt. 9, pp. 2474–2475.
E. J. Weber, "Compositions of Commercial Corn and Soybean Lecithins" JAOCS, Oct. 1981, pp. 898–901.

*Primary Examiner*—John W. Rollins
*Attorney, Agent, or Firm*—Meltzer, Lippe, Goldstein

[57] ABSTRACT

A phospholipid composition exhibiting a phosphatidylcholine content of at least 80% by weight is described. Whereby this pulverized or granulated composition is free from additives.

In order to prepare such a phospholipid composition the phospholipid starting material is comminuted after cooling to a temperature below −50° C.

14 Claims, No Drawings

PHOSPHOLIPID COMPOSITION

This invention relates to a phospholipid composition and to a process for the manufacture of such a phospholipid composition.

Phospholipids occur in both animal and vegetable matter and have to be isolated from these. The main sources are eggs, soybeans, oil seeds and oil fruit, such as coconut copra, palm kernels, groundnuts, rape, sunflower seeds, oil palms and olives.

Phospholipids are isolated from vegetable products by degumming the corresponding vegetable oil with, for example, a small quantity of steam or water. The phospholipid composition produced, also known as lecithin sludge, generally contains ca. 8 to 59% by weight phospholipids and is dried by various methods to yield crude lecithin on drying.

Depending on the initial lecithin sludge used in each case this crude lecithin will have a different chemical composition. Thus according to Weber E.J.; J.A.O.C.S. 58 898 (1981) the most important crude lecithin, soy (soybean) lecithin, is composed, after drying, of ca.:

| Triglycerides | 34.2% | phosphatidylcholine | 19.1% |
|---|---|---|---|
| Dilycerides | 0.4% | lysophosphatidylcholine | 0.7% |
| Free fatty acids | 0.4% | phosphatidylethanolamine | 8.6% |
| Other neutral lipids | 0.8% | phosphatidylinositol | 8.8% |
|  |  | phosphatidic acid | 4.2% |
| Glycolipids | 6.5% | N-acylphosphatidyl-ethanolamine | 1.0% |
| Carbohydrate | 6.7% |  |  |
|  |  | others | 8.6% |

Neutral lipids, such as, for example, triglycerides, diglycerides and the like, can be removed from the crude lecithin by deoiling with acetone. The deoiled crude lecithin, also referred to as pure lecithin, is a solid powder capable of being poured, which is available commercially as lecithin granules. The phosphatidylcholine content of pure lecithin lies between ca. 25% by weight and 30% by weight.

The phosphatidylcholine in crude lecithin or pure lecithin can be enriched by known processes. Preferably according to the processes described in European Patents 00 54 770 or 00 54 769. Hereby the crude lecithin is extracted with alcohol. The alcohol-soluble extraction phase is then chromatographed on silicon dioxide at elevated temperatures. On account of its high phosphatidylcholine content the phospholipid composition resulting from the aforesaid process is used for pharmaceutical, cosmetic and dietetic applications. However it exhibits the disadvantage that it is paste-like or waxy depending on its chemical composition. The further processing of this product is often accompanied by considerable problems on account of its consistency which makes it difficult to dose and causes it to stick to the inside walls of vessels, so that the residues remaining in the vessels make frequent and expensive cleaning of the vessels necessary.

In order to eliminate the aforesaid disadvantages in the handling of phospholipid compositions containing large proportions of phosphatidylcholine attempts have already been made to process these products in such a manner that powdered or granule-like high purity lecithins or specific high purity phospholipids are formed.

Thus German Patent 973 741 proposes deoiling crude lecithin with a suitable solvent, for example acetone, separating the deoiled lecithin from the oil extract, then loosening the separated lecithin and drying it as a thin layer. Thereafter the deoiled lecithin can be separated from the layer support used in the form of flocks or leaflets. However it is unlikely that such a process could be carried out nowadays at an economically acceptable cost. Furthermore the phosphatidylcholine content of 30% is too low for the applications described above.

Processes involving the use of additives are also known (U.S. Pat. Nos. 20 57 695 and 30 12 888).

A similar process has been proposed in German patent 38 26 946. Here a special sugar mixture (palatinit) is employed as an additive during the manufacture of the high purity phospholipid composition in order to yield powdered or granulated high purity specific phospholipids or phospholipid compositions.

However the aforesaid known methods possess the disadvantage that additional effort is involved, namely that it is necessary to add and work in an additive. Furthermore the phospholipid compositions prepared by the known methods are only of very restricted application on account of their relatively low phosphatidylcholine concentrations.

The present invention is intended to make available a phospholipid composition and a process for manufacturing such a phospholipid composition, that is particularly simple to carry out and leads to products which are stable on storage.

This intention is fulfilled by a phospholipid composition and by a process for the manufacture of such a phospholipid composition.

The phospholipid composition according to the invention with a phosphatidylcholine content of at least 80% by weight takes the form of a powdered or granulated composition and is, hence, free from additives of any sort.

The powdered or granulated phospholipid composition according to the invention exhibits a range of advantages. Thus it is particularly easy to handle on account of its granule-like or powdered consistency, so that the disadvantages described for the state of the art do not occur. Unexpectedly it was also found that the powdered or granule-like consistency is also maintained when the processing temperature of the powdered or granule-like composition rises to a temperature of about 30° C. The phospholipid composition also possesses long storage stability of up to several years without any changes occurring in the chemical or physical structure. This is particularly the case if the phospholipid composition is stored at a temperature below 10° C., preferably at a temperature between 1° C. and 6° C., preferably under an inert gas.

The aforesaid advantages of the phospholipid composition according to the invention mean that this composition is very readily applied to the manufacture of appropriate finished products, such as, for example, cosmetics, dietetic preparations or pharmaceutical preparations. This is on account of the fact that such powdered or granule-like compositions are particularly simply dosed and can be weighed out with great accuracy and reproducibility, which is not possible in the case of highly viscous or paste-like products. On account of the absence of additives (solidifiers) the composition according to the invention can also be applied where the known phospholipid compositions cannot be used on account of the additives they contain and/or their low phosphatidylcholine content, that is, in particular, for pharmaceutical products.

A particularly suitable embodiment of the composition according to the invention involves the composition according to the invention that, as has already been described, contains at least 80% by weight phosphatidylcholine, being predominantly crystalline. Especially when the composition according to the invention contains more than 80% by weight, and preferably more than 90%, crystalline phosphatidylcholine components, it is found that such a composition particularly possesses the aforesaid advantages that have been described in detail above. In other words such a composition according to the invention contains at least 64% by weight and preferably 72% by weight crystalline phosphatidylcholine components on an absolute basis. Unexpectedly it could be demonstrated that such a composition according to the invention, that preferably was composed primarily of crystalline components, is excellently dispersible in water, which, for example, considerably eases the manufacture of appropriate aqueous suspensions of cosmetic, dietetic or pharmaceutical preparations. The aforesaid ready dispersibility is unknown for phospholipid compositions according to the state of the art which is attributable to the fact that such known compositions are predominantly amorphous in nature.

A further embodiment of the composition according to the invention proposes that this possesses a concentration of at least 90% by weight phosphatidylcholine.

Another embodiment of the aforesaid composition contains the composition according to the invention 93% by wt. ±3% by wt. phosphatidylcholine and
3% by wt. ±3% by wt. lysophosphatidylcholine, whereby the aforesaid values have been checked by a known quantitative thin-layer chromatographic analysis method. Such a composition preferably does not contain any phosphatidylethanolamine and/or any phosphatidylinositol.

With respect to the particle size of the phospholipid composition according to the invention it may be said that this is adjusted according to the particular field of application. The phospholipid composition is preferably comminuted to a particle or crystallite size between 18 mm and 0.07 mm, particularly to a particle size between 6 mm to 0.5 mm.

The present invention also applies to a process for the preparation of the aforesaid phospholipid compositions.

The process according to the invention for the preparation of the powdered or granulated phospholipid composition starts out with an appropriate phospholipid composition, that, depending on its composition, possesses a pasty to waxy consistency under the usual conditions of storage. In this connection this phospholipid composition is comminuted to the desired powder or granule size while cooled to a temperature below $-50°$ C.

Unexpectedly it could be established that phospholipid compositions could be comminuted without problems under these temperatures without the need for admixture of the solidifying agents required in the known methods. In addition compositions that have been comminuted in this manner and that contain at least 80% by weight phosphatidylcholine are stable up to a temperature of 30° C. for several months and years so that chemical and physical changes do not occur.

A further specially favoured embodiment of the process according to the invention provides for the storage of the phospholipid composition at temperatures between $+5°$ C. and $-60°$ C., particularly at temperatures between $-10°$ C. and $-30°$ C. before comminution. Whereby the storage time varies between one day and 150 days, preferably between 30 days and 70 days depending on the storage temperature chosen. A phospholipid composition stored in the aforesaid manner can be comminuted to the initially mentioned particle size of 18 mm to 0.07 mm, preferably of 6 mm to 0.5 mm within a very short time.

Depending on the particular phospholipid composition employed a further method of execution of the process according to the invention involves the comminution and/or storage of the particular phospholipid composition at the aforesaid temperatures and for the aforesaid storage time under inert gas. In particular the inert gas can be liquid nitrogen, carbon dioxide, a noble gas or a mixture of the aforesaid gases. This method of operation under inert gas prevents an undesired oxidative modification of the phospholipid composition.

As already described above various highly purified phospholipid compositions isolated from natural products can be employed as starting materials for the process according to the invention, provided that they contain at least 80% by weight phosphatidylcholine. Such a composition can be isolated preferably from eggs, oil seeds and oil fruit and particularly soybean by the known procedures. However, it is particularly suitable when a soy (soybean) lecithin whose phosphatidylcholine content is at least 90% by weight and preferably 93±3% by weight is employed in the process according to the invention. Such a high purity soy lecithin can, for example, be isolated by the methods as they are described in the European patents 0 054 770 and 0 054 769.

In order to be able to store the powdered or granulated product prepared by the process according to the invention over a long period of time without chemical or physical change a further embodiment of the process according to the invention envisages storage at a temperature below 10° C. and preferably between 1° C. and 6° C.

A further improvement in the storage stability is achieved if the phospholipid composition is sealed into airtight sachets, for example of appropriate aluminium foil, and stored at the aforesaid temperatures.

A further embodiment of the aforesaid process envisages displacing the air contained in the sachets after they have been filled with an inert gas, for example, nitrogen, a noble gas, carbon dioxide or a mixture of the aforesaid gases.

As already described above the powdered or granulated phospholipid composition according to the invention is very easy to handle and can be employed for various purposes. Thus, for example, such a powdered or granulated phospholipid composition can be used as solution promoter, natural surfactant and/or liposome former in cosmetic products and especially in pharmaceutical products, since the phospholipid composition according to the invention is free from solidifying agents.

Advantageous filirther embodiments of the phospholipid composition according to the invention and the process according to the invention are set out in the subsidiary claims.

The process according to the invention is further illustrated by the examples that follow.

EXAMPLE 1

300 kg of a phospholipid composition containing 93% ±3% by weight phosphatidylcholine that, for example, had been isolated from soybeans according to the processes described in European patents 00 54 770 or 00 54 769 was stored at −20° C. for 2 months. Immediately before the phospholipid composition was comminuted it was brought to room temperature (17° C. to 21° C.). Then the composition was comminuted in a conventional cold milling plant with liquid nitrogen cooling and sealed portion wise in aluminium sachets under inert gas (nitrogen). The product that had been so packed was stored at +4° C.

Stability tests revealed that the product retained its powdered or granulated form at temperatures up to +30° C.

Immediately before such a product is processed it is warmed to room temperature to avoid the condensation of water onto the comminuted product.

EXAMPLE 2

As described above 100 kg of the aforesaid composition were comminuted in the cold. However in contrast to example 1 the storage time before comminution was one month at −17° C.

Stability tests revealed that there was no change in consistency even after storage for 12 weeks at room temperature (20° C. ±2° C.) after comminution and packing.

The powdered or granulated phospholipid composition so isolated had the following chemical composition:

| | |
|---|---|
| Phosphatidylcholine | 94.2% by wt. |
| Phophatidylethanolamine | not detectable |
| Phosphatidylinositol | not detectable |
| Lysophosphatidylcholine | 3.7% by wt. |
| Water | 1.3% by wt. |
| Trilycerides (oils) | 0.8% by wt. |

EXAMPLE 3

As previously described in example 1, 300 kg phospholipid composition were comminuted together with 150 kg carbon dioxide granules. Whereby the other conditions corresponded to those described in example 1.

Stability tests revealed that the composition prepared according to example 3, which contained the aforesaid high phosphatidylcholine content, also remained unchanged in consistency even on storage for six months after comminution.

We claim:

1. A process for the manufacture of a granulated phospholipid composition comprising
    cooling a phospholipid starting material having a phosphatidylcholine content of at least 80% by weight and is substantially free from additives to a temperature below −50° C., and
    comminuting said cooled phospholipid starting material until it has a particle size between 18 mm and 0.07 mm.

2. The process of claim 1 comprising comminuting said phospholipid starting material until it has a particle size between 6 mm and 0.5 mm.

3. The process of claim 1 further comprising storing said phospholipid starting material at a temperature between +5° C. and −60° C. before said comminuting step.

4. The process of claim 3 wherein said phospholipid starting material is stored or between one and 150 days before said comminuting step.

5. The process of claim 3 wherein said phospholipid starting material is stored for between one and 70 days before said comminuting step.

6. The process of claim 1 wherein said comminuting step is carried out under an inert gas.

7. The process of claim 3 wherein said storing step is carried out under an inert gas.

8. The process of claim 7 wherein said inert gas is nitrogen, carbon dioxide, a noble gas or a mixture thereof.

9. The processor of claim 3 further comprising warming said phospholipid starting material to room temperature after said storing step and before said comminuting step.

10. The process of claim 1 further comprising storing said phospholipid starting material at a temperature between −10° C. and −30° C. before said comminuting step.

11. The process of claim 1 wherein said phospholipid starting material is isolated from soy lecithin and contains 93±3% by weight phosphatidylcholine.

12. The process of claim 1 further comprising storing said phospholipid composition at a temperature of <10° C.

13. The process of claim 1 further comprising storing said phospholipid composition at a temperature of between 1° C. and 6° C.

14. The process of claim 13 wherein said phospholipid composition is stored under an inert gas.

* * * * *